(12) United States Patent
Pawlak et al.

(10) Patent No.: US 7,470,896 B2
(45) Date of Patent: Dec. 30, 2008

(54) NON-CIRCULAR-ORBIT DETECTION METHOD AND APPARATUS

(75) Inventors: John Thomas Pawlak, Villa Park, IL (US); Anthony Perrone, Crystal Lake, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 656 days.

(21) Appl. No.: 10/608,704

(22) Filed: Jun. 27, 2003

(65) Prior Publication Data

US 2004/0263865 A1    Dec. 30, 2004

(51) Int. Cl.
*G12B 13/00* (2006.01)
(52) U.S. Cl. .............................. 250/252.1; 250/363.05; 250/363.09
(58) Field of Classification Search ............ 250/363.05, 250/363.08, 363.09, 363.1, 252.1
See application file for complete search history.

(56) References Cited

U.S. PATENT DOCUMENTS

| | | | | |
|---|---|---|---|---|
| 4,503,331 A | * | 3/1985 | Kovacs et al. | 250/363.04 |
| 5,444,252 A | * | 8/1995 | Hug et al. | 250/363.08 |
| 5,677,535 A | * | 10/1997 | Stephan | 250/363.02 |
| 5,691,538 A | * | 11/1997 | Ohike et al. | 250/363.05 |
| 5,777,332 A | * | 7/1998 | Lonn et al. | 250/363.04 |
| 5,811,813 A | * | 9/1998 | Maor | 250/363.05 |
| 6,020,589 A | * | 2/2000 | Plazenet et al. | 250/363.04 |
| 6,147,353 A | * | 11/2000 | Gagnon et al. | 250/363.05 |
| 6,204,503 B1 | * | 3/2001 | Pierfitte et al. | 250/363.05 |

\* cited by examiner

*Primary Examiner*—David P. Porta
*Assistant Examiner*—David S Baker

(57) ABSTRACT

A non-circular-orbit detection method and apparatus is disclosed. In some embodiments, the method includes: locating first and second detectors, displaced with respect to one another, a distance from a patient; moving the first and second detectors in a direction towards the patient until a first sensor senses a first point of the patient at a first sensing position; moving the first and second detectors in a second direction from the first sensing position until a second sensor senses a second point of the patient at a second sensing position; and moving the first and second detectors in a non-circular-orbit around the patient. Preferably, the method includes determining the non-circular-orbit based on, among other things, locations of the first point and the second point.

25 Claims, 7 Drawing Sheets

NON-CIRCULAR-ORBIT DETECTION METHOD AND APPARATUS

BACKGROUND

1. Field of the Invention:

The present invention relates to methods and apparatuses for scanning a body and preferred embodiments relate, more particularly, to methods and apparatuses for determining a non-circular-orbit for scanning a patient.

2. Discussion of the Background:

In some existing systems, gamma cameras are used to form tomographic images of a patient during a nuclear medicine study. In, for example, single photon emission computed tomography (SPECT) systems of the transaxial rotational camera type, a scanning gamma camera head can rotate around a region of the patient to be scanned. Typically, this rotation is in a plane generally orthogonal to a cranial-caudal axis of a patient and results in the imaging of a cross-sectional slice of the patient's body.

In general, for certain detectors, such as, e.g., parallel hole collimated detectors, resolution decreases with distance so that keeping the detector close to the patient can improve resolution and image quality. As addressed by the present assignee in U.S. Pat. No. 5,523,571, it can be desirable for a camera head to be close to a patient's body because this results in increased sensitivity and, consequently, a better image (if the length of the study is held constant) or a shorter study (if the image quality is held constant). In some systems, the orbit of the camera head has been made non-circular with respect to a patient to decrease the average distance between the camera head and the patient.

A few illustrative devices for producing a non-circular orbit are disclosed, e.g., in U.S. Pat. No. 4,503,331 (entitled Non-Circular Emission Computed Tomography), showing, e.g., a "radiation imaging system [that] includes a rotatable scintillation detector and a linearly movable detector stand" and U.S. Pat. No. 4,593,189 (entitled Proximity Detector For A Body Scanner), showing, e.g., "an energy beam emitting and receiving device in front of the scanning surface of the body scanner for an energy beam projected in a plane parallel to the scanning surface" and "[a] signal generator . . . connected with the energy beam emitting and receiving device for generating a proximity signal when the energy beam becomes weakened or interrupted." See Abstracts.

A few existing methods for accomplishing non-circular-orbits for nuclear medicine cameras are now discussed with reference to FIGS. 7(A), 7(B) and 7(C).

With reference to FIG. 7(B), a first method is referred to as a "manually operated learn mode" method. In this method, a nuclear medicine technologist can pre-program an orbit by first manually moving the detector adjacent to a patient at a standard position (e.g., at 9:00 o'clock and 12:00 o'clock positions). The camera then calculates the orbit based on these manually determined positions. Then, the camera follows the calculated orbit during acquisition. One disadvantage of this type of method is the time required to move the detector to the standard position. In addition, because the pre-programming is performed manually, the likelihood of error is large.

With reference to FIG. 7(A), a second method for accomplishing a non-circular-orbit is referred to as an "auto-contour" method. As shown in FIG. 7(A), in this method, two rows of light beams are employed. The two rows of light beams b1 and b2 are used on each detector to maintain proximity to the patient P by maintaining the patient continuously between the rows of light beams as shown in FIG. 7(A). Among other things, this method has disadvantages related to the potential of creating sharp changes in the resolution during operation. In addition, the quality of the image deconstruction can be degraded by sharp jumps in image resolution from view to view. In addition, with dual detector systems that are reconfigured to, e.g., 90 degrees, there is what is known as the "dead zone" between detectors (see, for reference, zone Z in FIG. 4). When using an "auto-contour" method, to address the presence of a "dead zone," it has been necessary to conduct a pre-scan around a patient P (see, e.g., FIG. 7(C)) to trace the non-circular-orbit, to add an offset, and then to execute the actual scan. Among other problems, a pre-scan adds a significant amount of time.

In addition to the foregoing, some illustrative methods and apparatuses are shown by way of example in the following references: (1) U.S. Pat. No. 6,255,656 entitled "Positioner for a Scintillation Camera Detector Head;" (2) U.S. Pat. No. 6,150,662 entitled "Gantry for Medical Imaging System;" (3) U.S. Pat. No. 6,114,701 entitled "Configurable Multiple Detector Nuclear Medicine Gantry;" (4) U.S. Pat. No. 6,055,450 entitled "Bifurcated Gamma Camera System;" (5) U.S. Pat. No. 5,929,446 entitled "Configurable Multiple Detector Nuclear Medicine Gantry;" (6) U.S. Pat. No. 5,866,906 entitled "Gamma Detector Locking Mechanism;" (7) U.S. Pat. No. 5,838,009 entitled "Variable Angle Multiple Detector Nuclear Medicine Gantry;" (8) U.S. Pat. No. 5,760,402 entitled "Dual-Head Medicine Imaging System With Cantilevered Detector Heads;" (9) U.S. Pat. No. 5,742,060 entitled "Medical System for Obtaining Multiple Images of a Body From Different Perspectives;" and (10) U.S. Pat. No. 5,523,571 entitled "Versatile Reconfigurable Gantry for Use In Scintillation Camera Systems." All of the patents cited in this application are incorporated herein by reference in their entireties.

While a variety of methods and apparatuses are known, there remains a need for improved methods and apparatuses overcoming the above and/or other problems.

BRIEF DESCRIPTION OF THE DRAWINGS

The preferred embodiments of the present invention are shown by a way of example, and not limitation, in the accompanying figures, in which.

SUMMARY OF THE INVENTION

Figure 1:
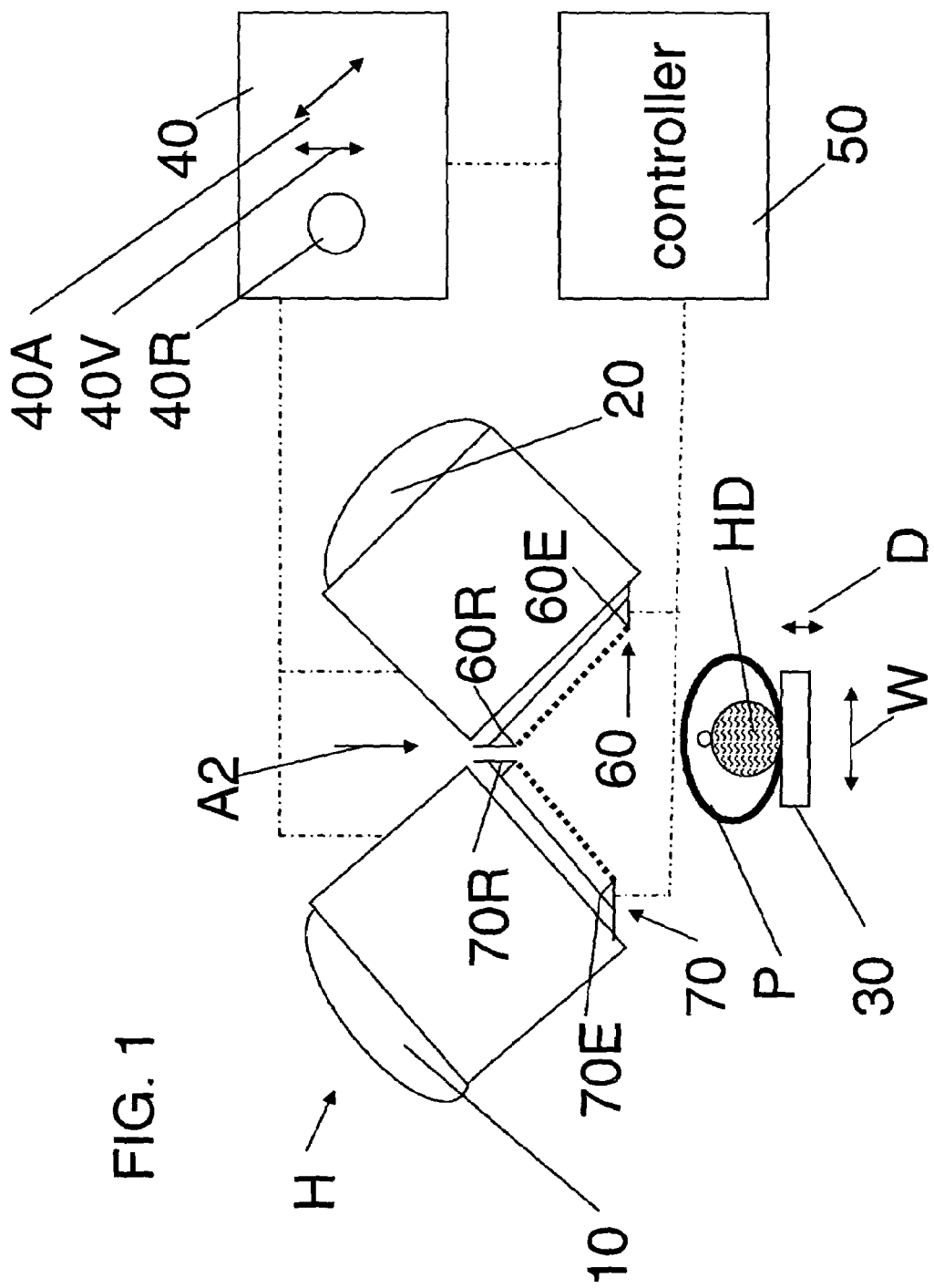
FIG. 1 shows an apparatus according to a first embodiment of the invention in an initial position over a patient.

The preferred embodiments of the present invention can significantly improve upon existing methods and/or apparatuses.

According to some embodiments of the invention, a non-circular-orbit detection method is provided that includes: locating first and second detectors, displaced with respect to one another, a distance from a patient; moving the first and second detectors in a direction towards the patient until a first sensor senses a first point of the patient at a first sensing position; moving the first and second detectors in a second direction from the first sensing position until a second sensor senses a second point of the patient at a second sensing position; and moving the first and second detectors in a non-circular-orbit around the patient. Preferably, the method includes determining the non-circular-orbit based on, among other things, locations of the first point and the second point. In preferred embodiments, the detectors include nuclear medicine detectors. Preferably, the method includes locating the first and second detectors at an angle with respect to one another. In preferred embodiments, the first direction is generally downward and/or the second direction is generally parallel to a front of the first detector. Preferably, the first and second sensors emit light beams that are broken by proximity to a patient.

According to other embodiments of the invention, a method for orbital detection is provided that includes: a) moving, relative to a patient, a first detector in a first direction between a position distal to the patient and a position adjacent to the patient based on an output of a sensor that senses patient proximity to the first detector; b) moving a second detector, relative to a patient, in a second direction between a position distal to the patient and a position adjacent to the patient based on an output of a sensor that senses patient proximity to the second detector; and c) determining an orbital path of the first and second detectors around the patient based upon the position adjacent to the patient in part a) and the position adjacent to the patient in part b). In preferred embodiments, the method further includes performing the moving in parts a) and b) automatically. Here, the language "moving, relative to the patient," is defined herein to mean that the relative position of the detector to the patient is are changed, such that, e.g., movement could be carried out in whole or in part by actually moving the patient relative to the detector.

According to other embodiments of the invention, an orbital-detector apparatus is provided that includes: a) a first detector element to detect inside a patient; b) a first sensor element to sense patient proximity to the first detector element; c) a second detector element to detect inside the patient; d) a second sensor element to sense patient proximity to the second detector element; e) a first carrier mechanism configured to move the first detector element in a first direction from a position distal to the patient to a position adjacent to the patient based on an output of the first sensor element; f) a second carrier mechanism configured to move the second detector element in a second direction from a position distal to the patient to a position proximate to the patient based on an output of the second sensor element; g) a control unit configured to determine an orbital path of at least one of the first detector element and second detector element around the patient based upon the position adjacent to the patient in part e) and the position adjacent to the patient in part f). Preferably, the apparatus varies a radius of the orbital path to reduce a distance of the first and second detector elements from the patient. Preferably, at least one of the first detector element and the second detector element includes a parallel-hole collimated detector.

According to other embodiments of the invention, a non-circular-orbit detector is provided that includes: first and second detector elements arranged in a generally V-configuration with the first detector element extending along one leg of the V-configuration and the second detector element extending along another leg of the V-configuration; means for moving the first and second detector elements, relatively to a patient, such that an open end of the V-configuration moves towards the patient until a sensor senses when the first detector element is adjacent a first point of the patient; and means for moving the first and second detector elements, relatively to the patient, generally parallel to the one leg of the V-configuration until a sensor senses when the second detector element is adjacent a second point of the patient. Here, the language "moving the . . . elements relatively to the patient" is defined herein to mean that the relative position of the elements to the patient is are changed, such that, e.g., movement could be carried out in whole or in part by actually moving the patient relative to the elements. In preferred embodiments, the detector includes means for moving the first and second detectors in a non-circular orbit about the patient based on the first and second points.

According to other embodiments of the invention, a method for nuclear medicine detection with at least one nuclear medicine detector that follows a non-circular orbit, comprising: a) automatically determining a plurality of locations around a perimeter of a patient without a detector pre-scan; b) automatically determining a non-circular orbit around a patient based, at least in part, upon the plurality of locations; c) moving at least one nuclear medicine detector along the non-circular orbit around the patient for acquisition of nuclear medicine data. Preferably, the automatically determining in a) includes sensing the proximity to a patient of at least two detectors which are arranged in a V-configuration during data acquisition. Preferably, the automatically determining in b) includes calculating a non-circular orbit using a controller. In addition, the automatically determining in a) preferably includes establishing at least one location based on at least one location against which the patient is supported.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

DETAILED DESCRIPTION OF THE PREFERRED EMBODIMENTS

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

In some preferred embodiments of the invention, the system can achieve advantages beyond prior methods while avoiding disadvantages therein. The preferred embodiments of the invention can be employed in a variety of environments and can, e.g., be used in whole body, cardiac and/or general SPECT studies and/or can be useful in, e.g., various general purpose, cardiology, oncology and/or neurology studies.

With reference to FIG. 1, some illustrative embodiments of the invention include: a first detector element 10; a second detector element 20; a support 30 upon which a patient P can rest; a carrier mechanism 40 that effects movement of the detectors; a controller 50 that controls the carrier mechanism 40; a first sensor element 60; and a second sensor element 70.

In some preferred embodiments, the first and second detector elements can include separate detectors. In some preferred embodiments, the two separate detectors are nuclear energy detectors, such as, e.g., gamma detectors. Preferably, the detectors include parallel-hole collimated detectors.

In some preferred embodiments, the support 30 includes an elongated platform upon which a patient P can lay in a generally reposed orientation, such as, e.g., generally horizontal. In the illustrated embodiment, by way of example only, the patient P is shown lying upon the support looking upward (i.e., the top of the patient's head HD being shown). In preferred embodiments, the support has a narrow width W and depth D such as to avoid interference with the detector elements during operation. In some embodiments, the support 30 can include structure similar to that disclosed in one or more of the patents incorporated herein by reference above.

In some preferred embodiments, the carrier mechanism 40 can include one or more sub-carrier for effecting rotational movement of the detector elements (such as, e.g., 40R) and reciprocal movement of the detector elements (such as, e.g., 40V and 40A). In the illustrative example, the reciprocal movement 40V is preferably generally vertical and the reciprocal movement 40A is preferably at an angle to the vertical (such as, e.g., at an angle corresponding to one-half of the angle between the detector elements in some embodiments). The mechanism 40 can include any appropriate mechanism known in the art to effect desired movements. By way of example, the mechanism 40 can employ linear bearing tracks or guides for effecting linear movement in desired directions and/or rotary tracks or guides for effecting rotational movement. Additionally, the carrier mechanism 40 could employ one or more robot arm to adjust a position and/or orientation of a particular detector element. By way of example, the carrier mechanism 40 can include components similar to that disclosed in any of the above patents incorporated herein by reference. In addition, the carrier mechanism 40 can include components similar to that used in one or more of the following existing nuclear medicine detector systems: the SIEMENS model E.CAM gamma camera (which allows, e.g., various detector angle configurations, such as, e.g., 180E, 90E and/or 76E detector configurations to optimize image quality), enables both rotational and reciprocal movement of detectors, provides motion flexibility, including caudal/cephalic detector tilt, etc.; the GENERAL ELECTRIC models MILLENIUM VG HAWKEYE and/or INFINIA; and/or the PHILIPS model FORTE. In some preferred embodiments, the detector elements 10 and 20 can be independently moved and/or dependently moved together in unison (such as, e.g., being linked together and/or fixed relative to one another).

Figure 6:
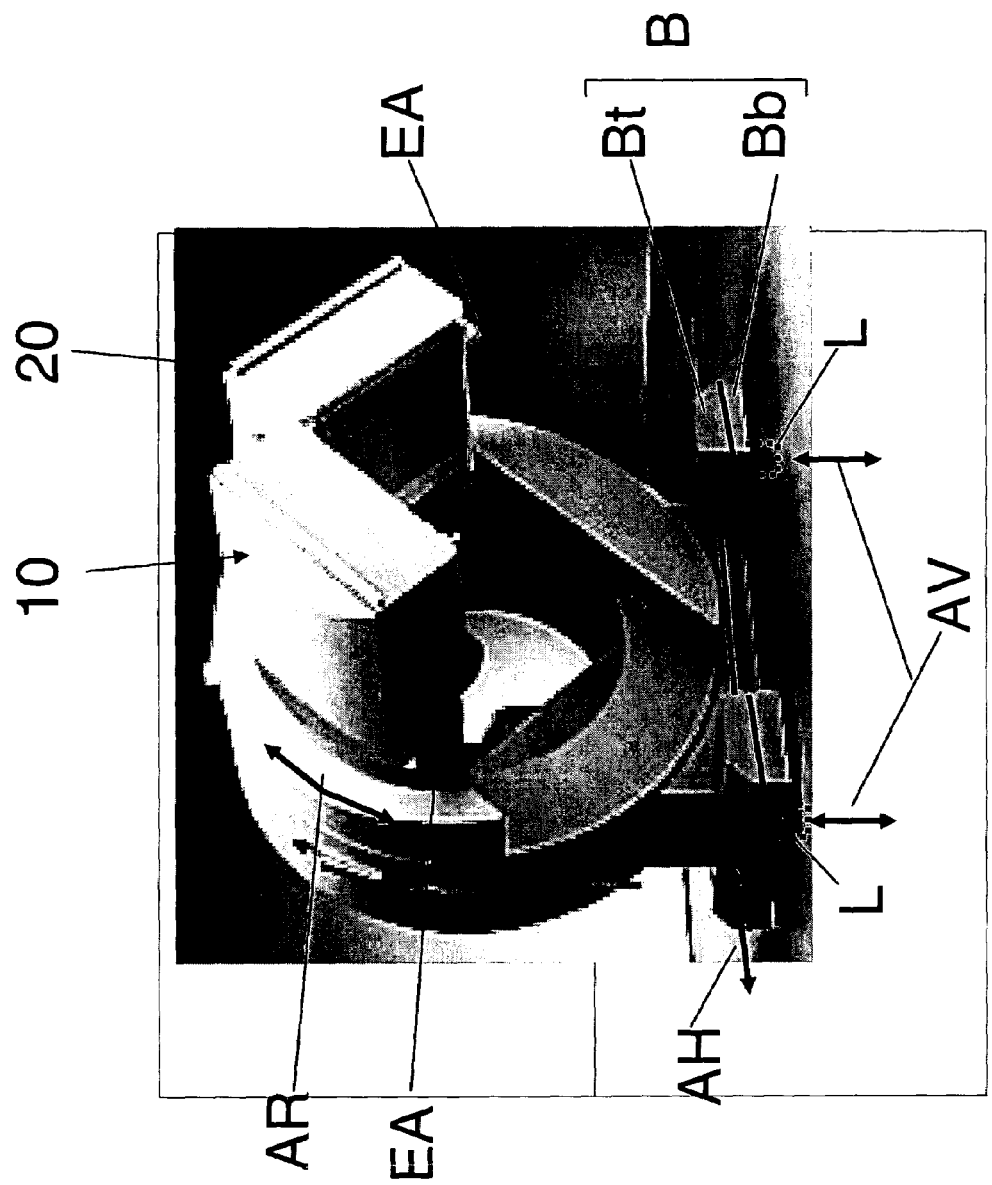
FIG. 6 is an elevational view of a gantry in which some illustrative embodiments of the present invention may be implemented.

In some embodiments, the carrier mechanism can include structure similar to that depicted in FIG. 6. The device shown in FIG. 6 can be, e.g., constructed as a modified SIEMENS model E.CAM. In this regard, the device can include one or more detector elements (in the illustrated embodiment, two detector elements 10 and 20 are shown) that are rotatably mounted so as to move rotatably around the O-shaped gantry as depicted by arrows AR. In some embodiments, the rotation can be partially around the O-shaped gantry. In other embodiments, the rotation can be fully around the O-shaped gantry. In some preferred embodiments, the detectors can be mounted upon extension arms EA that are pivotally mounted to the gantry to allow the detector(s) to be moved to and/or from a center-line of the O-shaped gantry. In some illustrative embodiments, a base B supporting the gantry can include a top portion Bt that is movably mounted over a bottom portion Bb (such as, e.g., in a generally horizontal reciprocating path AH). In some embodiments, a sub-carrier mechanism can be provided that effects lateral movement of the top portion Bt with respect to the bottom portion. In some embodiments, this lateral movement can be carried out, by way of example only, via motor operated screw-shafts, linear bearings, hydraulic cylinders, timing belts, stepper motors and/or any other appropriate components to effect such movement. In some illustrative embodiments, a sub-carrier mechanism can be provided that effects upward and/or downward movement of the gantry. By way of example, at least one lift L can be included (such as, e.g., beneath the base B as shown in dashed lines) so as to impart a generally vertical motion to the gantry. In some illustrative embodiments, this generally vertical motion can be carried out, by way of example only, via motor operated screw-shafts, linear bearings, hydraulic cylinders, timing belts, stepper motors and/or any other appropriate components to effect such movement. In the illustrative and non-limiting embodiments shown in FIG. 6, the carrier mechanism can provide the desired motions for at least some of the embodiments of the invention described herein. For example, in some preferred embodiments, the device shown in FIG. 6 can effect desired motions based on, e.g., motions in the directions AR, AH, AV and/or via the extension arms EA. In the preferred embodiments, these motions can be independently controlled and/or operated, such as, e.g., by employing independent drive sources that may be independently controlled (such as, e.g., via the controller 50). As a result, the device can effect generally vertical movement (such as, e.g., AV as shown), an angular movement (such as, e.g., via a controlled combination of, e.g., AH and AV movements) and can generate a desired non-circular orbit (such as, e.g., via a controlled combination of, e.g., AH, AV, AR and/or EA movements).

In some preferred embodiments, the sensor elements 60 and/or 70 can include light beam sensors. In this regard, the sensor elements can include, light emitters (such as, e.g., 60E and 70E) and light receivers (such as, e.g., 60R and 70R) that transmit and receive light beams, respectively, as shown in dotted lines in FIG. 1. Preferably, the sensor elements 60 and/or 70 output a signal (e.g., identifying the sensing of an event) upon the breaking of a sensed light beam. Preferably, the sensor elements 60 and/or 70 include a row of light beam emitters and receivers arranged in a plane in front of the respective detector elements. In this manner, the sensors 60 and/or 70 preferably detect whether or not something, such as, e.g. a patient projects within a plane sensed by the respective sensor. While light beam sensors are used in some illustrative and non-limiting embodiments, any sensor devices may be employed in other embodiments, as long as the sensors 60 and/or 70 can detect that the presence of a patient in proximity to the detector elements. By way of example, the sensors 60 and/or 70 could employ laser detection techniques, ultrasonic detection techniques, thermal detection techniques and/or any other means for detection of the position of a patient. In some preferred embodiments, the sensor elements can be mounted upon heads H containing the detector elements. In other embodiments, the sensor elements can be located proximate thereto as long as the proximity between the detector elements (e.g., the heads H) and the patient P is detected.

As schematically depicted in FIG. 1, a controller 50 is preferably provided that can be used to control the operation of the carrier mechanism 40 based upon output from the sensor elements 60 and/or 70. In some illustrative embodiments, the controller 50 can include a computer processor and/or any other appropriate control unit. Preferably, the controller 50 operates such that the operation of the system is substantially or entirely automated. However, in some less preferred embodiments, one or more steps can be effected and/or facilitated by a user of the system. For example, in some embodiments, the sensors 60 and/or 70 can be configured to set off an alarm to notify a user to stop the position of the detector elements. In addition, various steps could potentially be initiated by a user (for example, a user may be allowed and/or required in some embodiments to indicate when the system should proceed from one step to another in the operation of the system, such as related to, e.g., some of the illustrative steps discussed below).

In some preferred embodiments, the device shown in FIG. 1 can operate as follows.

In a first step (such as, e.g., shown in FIG. 1), the detector elements can be positioned above or otherwise displaced from a patient. For example, in some less preferred embodiments, the detector elements can be laterally displaced to a side of a patient. In this regard, the two detector elements are preferably arranged in a V-configuration (e.g., arranged at an angle to one another) with the open end of the V-configuration facing the patient. In some preferred embodiments, the angle can be between about 45 degrees and 135 degrees. In some preferred embodiments, the angle can be about 76 degrees, about 90 degrees or about 180 degrees. In the illustrated examples, the angle is about 90 degrees.

In a second step (such as, e.g., shown in FIG. 2), the detector elements are preferably moved downward in the direction of the arrow A2 shown in FIG. 1 until one of the light beams of a sensor element associated with a detector element is broken. Preferably, the detector elements are moved in a fixed relationship to one another such that they are moved in this second step in unison. Alternatively, the first and second detector elements can be individually and/or independently moved in some embodiments of the invention. Once a first of the detectors reaches a point at which a sensor senses proximity (such as, e.g., once a light beam is broken in the illustrated embodiment), the system can proceed to the next step.

Figure 2:
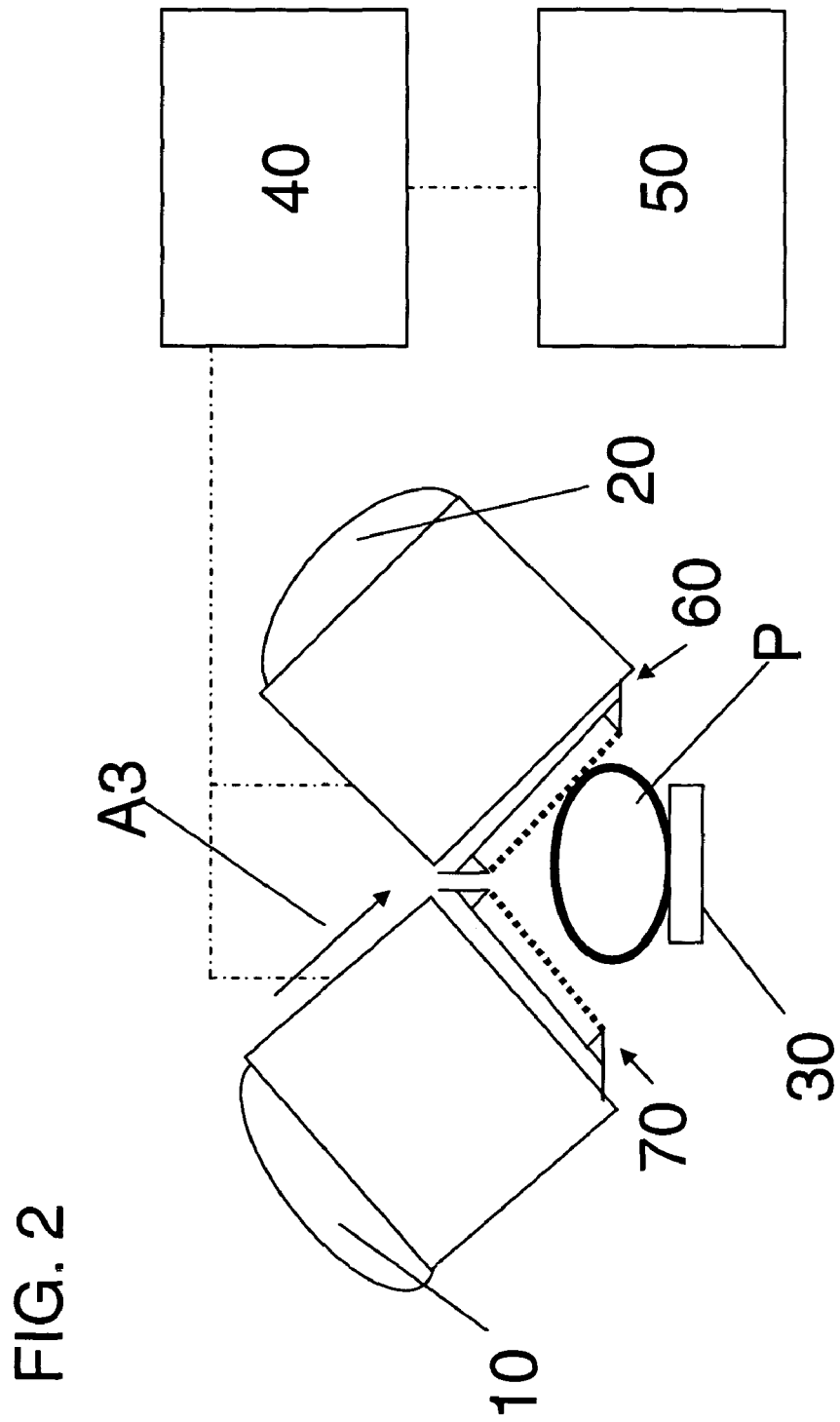
FIG. 2 shows the apparatus of FIG. 1 in a first sensor sensing position adjacent the patient.

In the third step (such as, e.g., shown in FIG. 3), the detector elements are preferably moved downward at an angle A3 shown in FIG. 2 (such as, e.g., at a 45 degree angle in the illustrated embodiment in which the detectors are at a 90 degree angle from one another) until a second sensor element detects proximity to a second point of a patient (preferably, e.g., when a light beam of a second sensor is broken). Preferably, the detector elements are moved in a fixed relationship to one another such that they are moved in this second step in unison. Alternatively, the first and second detector elements can be individually and/or independently moved in some embodiments. After the first of the detector elements reaches a point at which a sensor senses proximity (such as, e.g., once a light beam is broken in the illustrated embodiment), the system can proceed so as to move at least the second of the detector elements until the second sensor element detects proximity in this step.

In a fourth step, the system preferably processes information obtained based on the foregoing to ascertain a desired orbital path for the detectors to follow during acquisition. In this regard, at reaching this fourth step, the system can thereby "know" three tangent lines to the patient. Accordingly, the detector may calculate an optimal non-circular-orbit profile based upon knowledge of these three tangential lines-namely, a first tangent line based on a point detected by the first detector element, a second tangent line based on a point detected by the second detector element and a third tangent line based on established position of the patient (such as, e.g., based on knowledge of the patient's position vis-a-vis the surface of the support 30 upon which the patient rests in some embodiments). In this regard, the calculation can, thus, be based on, among other things, the two detected lines or points adjacent the patient in the foregoing steps.

In preferred embodiments, upon determining three tangential lines or points to a patient, the system can be configured to calculate an optimal non-circular orbit, such as, e.g., an ellipse or another shape based upon the determined three tangential lines or points. In some embodiments, the shape can be based upon empirical patient data used to provide an estimation of patient shape based upon closeness of the measured tangential lines and/or points. In some preferred embodiments, the controller 50 can be configured to calculate the desired orbit. In other embodiments, another computer, processor, controller and/or the like could be used to determine the desired orbit.

In some embodiments, the system can be configured to modify the orbit based on conditions, such as, e.g., based on measurements determined. For example, if the patient is detected as being too small, then it may be desirable to modify the non-circular orbit such as to move the detector elements further outward prior to initiation of the acquisition step so as to help keep the small patient (such as, e.g., a child) outside of a zone Z (shown in dotted lines in FIG. 4) at a juncture between adjacent detectors (e.g., which zone can have lower detection qualities in, e.g., nuclear medicine detectors).

Figure 3:
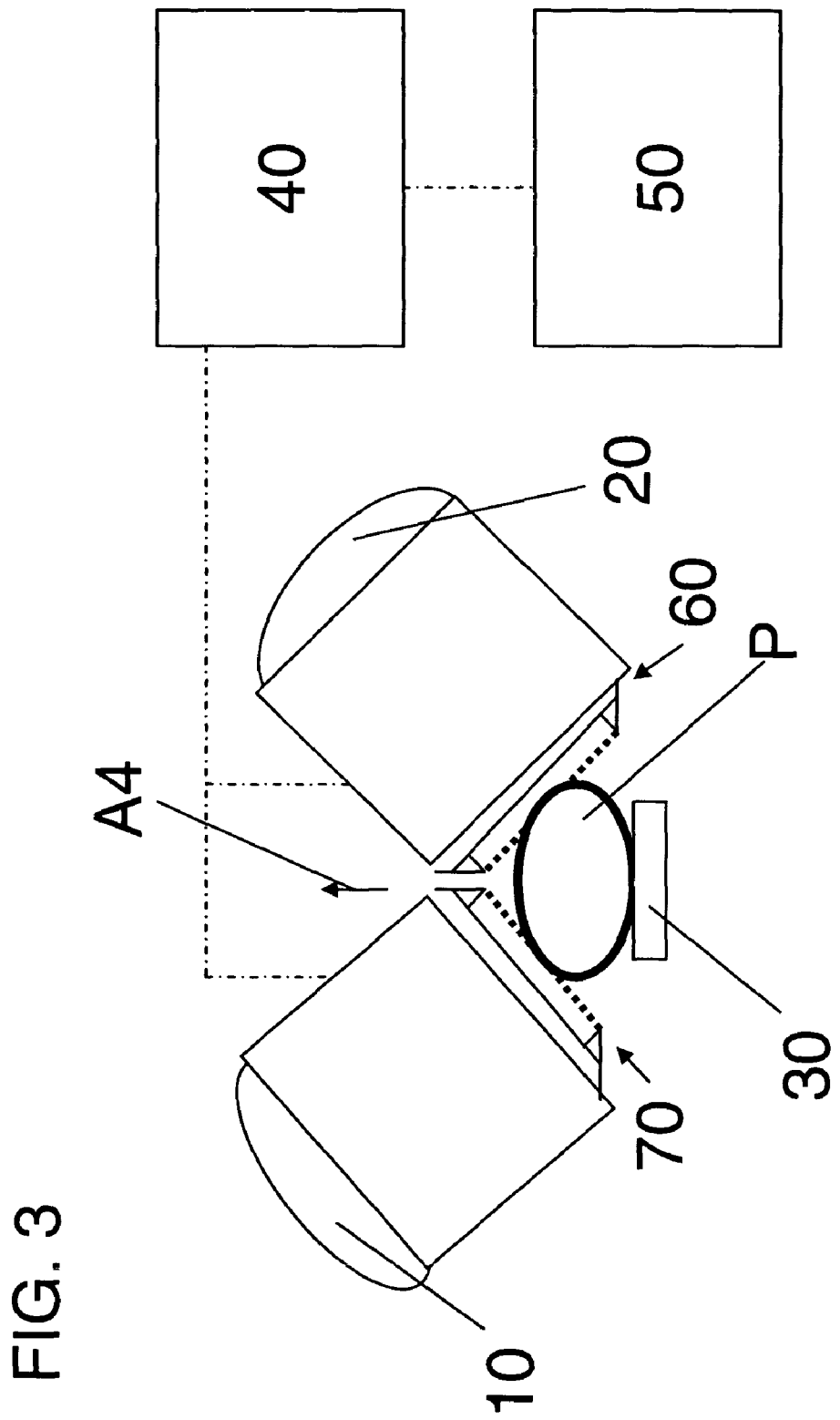
FIG. 3 shows the apparatus of FIG. 1 in a second sensor sensing position adjacent the patient.

In a fifth step (such as, e.g., shown in FIG. 4), the system can, if desired, be adapted to move the detector elements upwards, such as, e.g., in the direction of the arrow A4 shown in FIG. 3, a pre-determined amount away from the patient so as to maintain a desired distance during scanning. By way of illustration, the system could be adapted to move upward about ¼ inch before acquisition scanning. Among other things, this can help to ensure that the patient does not contact the device. Additionally, in some embodiments, the system can be configured to move the detector elements away from the patient based upon some sensed conditions. For example, during operation, in some embodiments, the system can be configured to adapt to sensed conditions, such as, e.g., sensed anomalies. For example, if during scanning the first or second sensor elements sense the presence of an object (such as, e.g., having a broken sensor beam), the system can be adapted to move that respective sensor away from the patient (e.g., until a non-sensed condition occurs). This can, e.g., help the system to adapt to irregularities of a patient (such as, e.g., if a patient has an item in his or her pocket), to movement of a patient (such as, e.g., if a patient moves his or her arms during scanning), etc.

Figure 5:
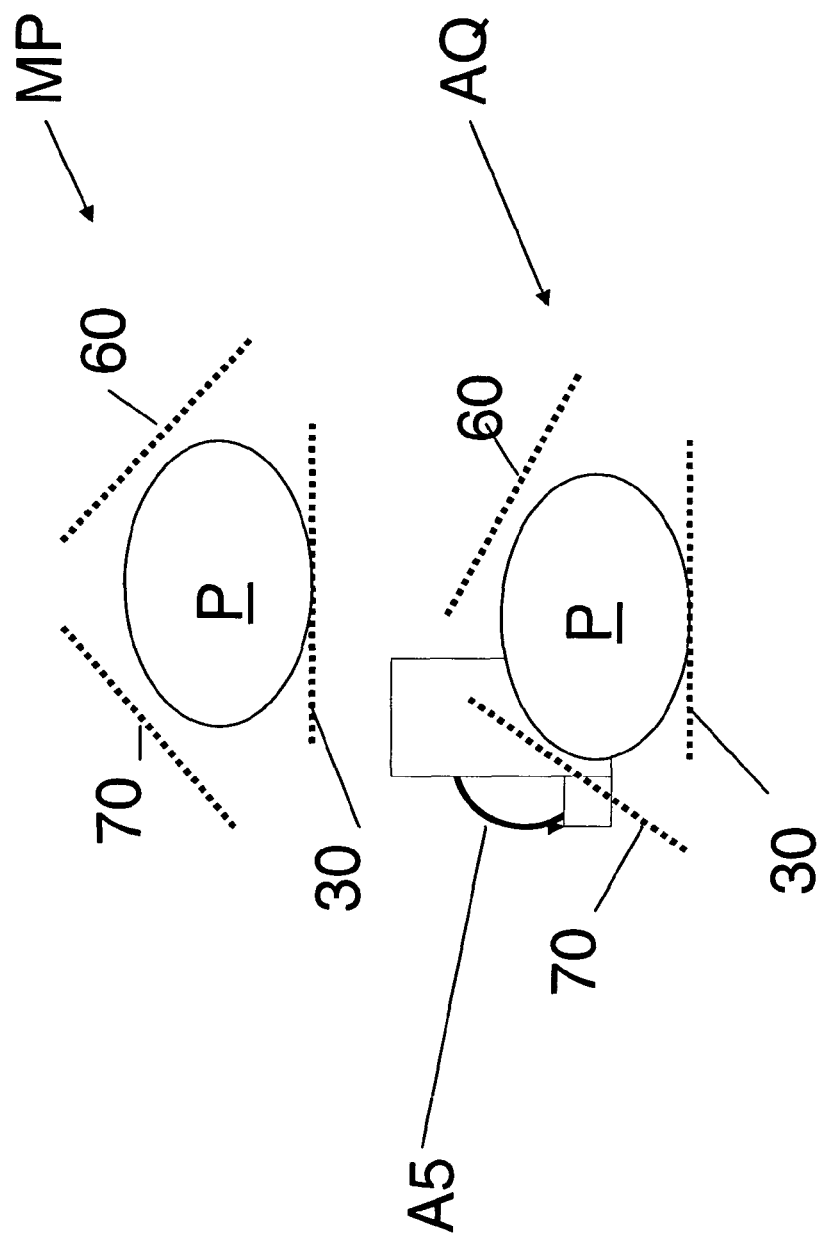
FIG. 5 is a schematic diagram showing rotation of detector positions in some illustrative embodiments of the invention.

In a sixth step (such as, e.g., schematically shown in FIG. 5), the system can be used to effect acquisition. In this regard, the detector elements can be driven (such as, e.g., via the carrier mechanism 40 and the controller 50) around the patient P along at least a portion of the determined non-circular orbit. FIG. 5 schematically depicts an illustrative measuring position MP in which the sensor elements 60 and 70 and the patient support 30 are located to determine a desired orbit and in an illustrative acquisition position AQ in which the sensor elements 60 and 70 are shown rotated about the patient P in the direction of the arrow A5.

While in some illustrative embodiments, as shown, two detector elements (such as, e.g., detector elements 10 and 20) are employed, other embodiments can employ one detector element and/or more than two detector elements. While two tangent points to a patient are preferably determined in some preferred embodiments, other embodiments can include a determination of another number of tangent points and/or patient perimeter points. For example, in some embodiments, three or more tangent points can be determined. In some embodiments, if the number of tangent points to be determined is greater than the number of detector elements, one or more of the detector elements can be moved to determine multiple tangent points. For example, in some illustrative single detector element embodiments, the single detector element could be moved to detect a first patient tangent point, and then moved from the first point to detect a second patient tangent point.

In some preferred embodiments, the present invention can, if desired, achieve some notable advantages over existing systems and methods, such as, by way of example, one or more of the following advantages.

First the preferred embodiments can achieve very reliable results. For example, the preferred embodiments can include a low likelihood of error because no manual positioning of the detector elements is required in the preferred embodiments.

Second, the preferred embodiments can operate very quickly. For example, the preferred embodiments can avoid the need for slow manual positioning of detectors. Moreover, the preferred embodiments can eliminate the time consuming requirement of pre-scanning. Moreover, in some preferred embodiments, a non-circular-orbit scan can start from the position or rotate angle that the measurement is made from—e.g., the detectors can be efficiently rotated from their detector positions at the time of measurement.

Figure 7A:
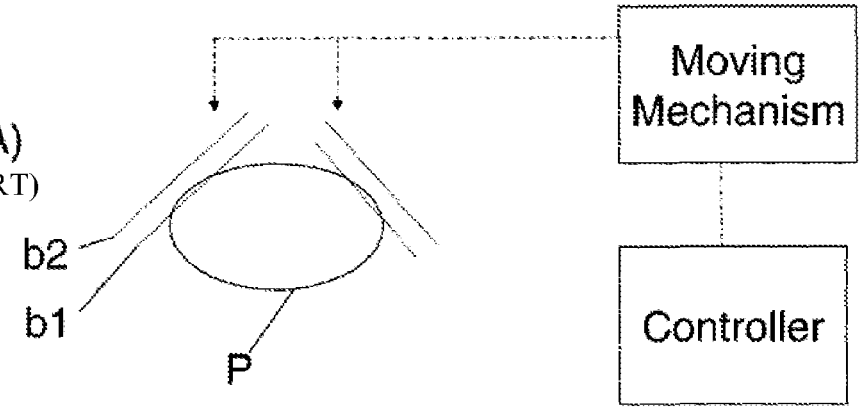
FIGS. 7(A), 7(B) and 7(C) are schematic diagrams used for describing some background systems.
Figure 7B:
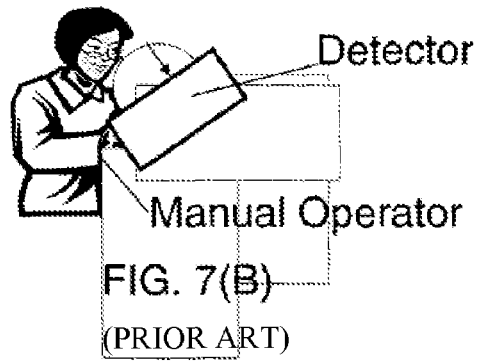
Figure 7C:
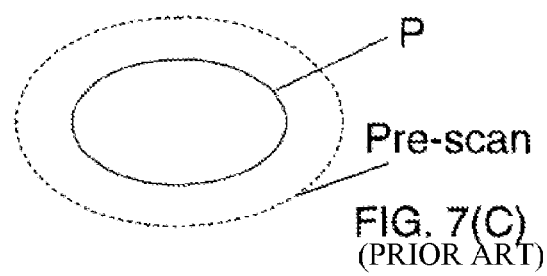

Third, in the preferred embodiments, resolution jumps can be eliminated. In this regard, in some embodiments, because a smooth non-circular orbit can be calculated based upon the detected tangent lines or points, the sharp resolution jumps that occurred in background systems such as, e.g., that depicted schematically in FIG. 7(A) can be avoided.

Figure 4:
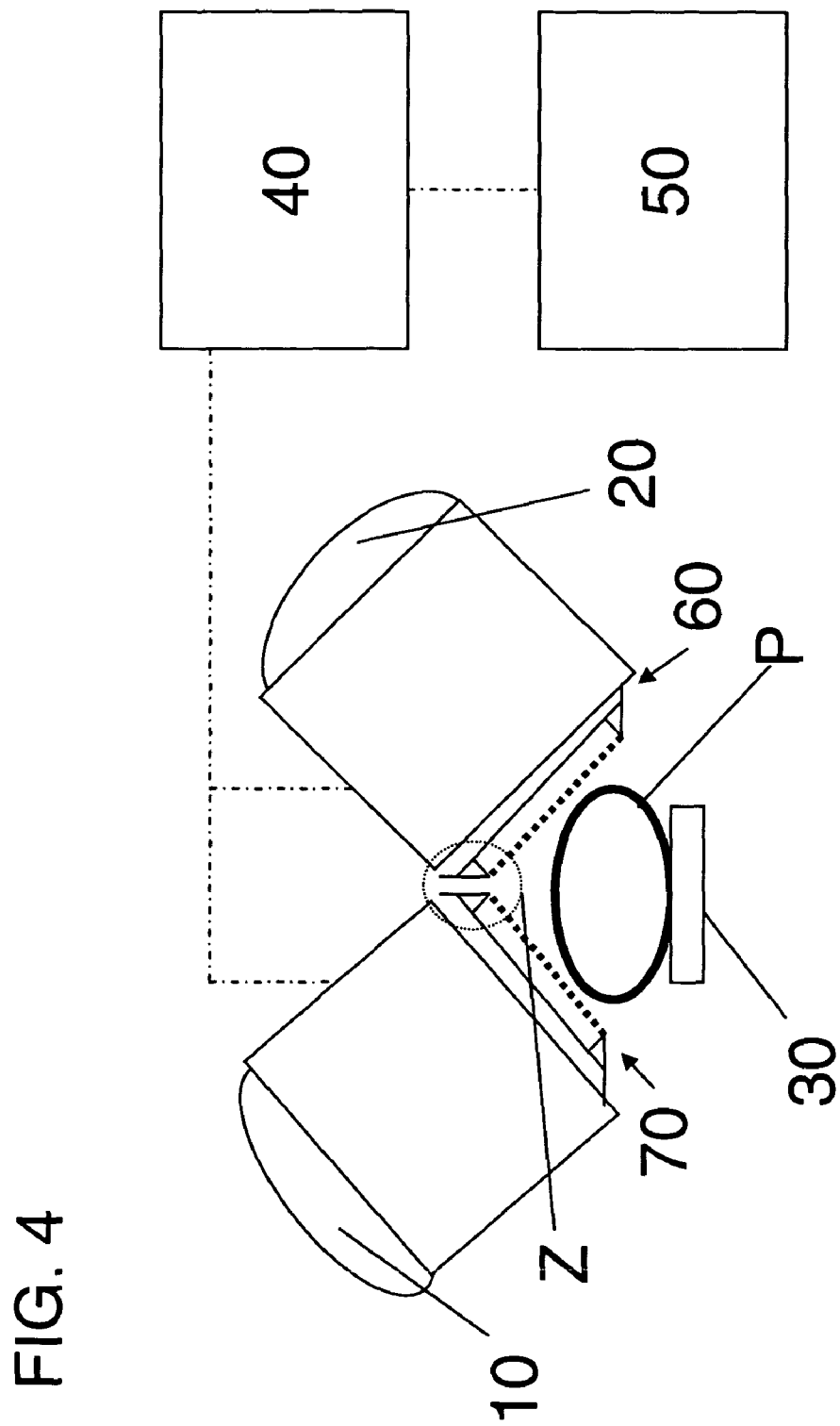
FIG. 4 shows the apparatus of FIG. 1 in a position separated from the patient.

Fourth, in some embodiments, there is a new ability to account for the presence of a dead zone (such as, e.g., zone Z shown in FIG. 4). For example, in some embodiments, a dead zone calculation can be made immediately before a scan begins (such that, e.g., adjustments can be made in some cases). In addition, the calculation can be varied depending on, for example, the reconfiguration angle.

Fifth, in some embodiments, the system can be implemented at a very low cost. For example, in some previous implementations, "auto contour" non-circular-orbit implementations required two rows of light beams (such as, e.g., shown in FIG. 7(A)). On the other hand, in some preferred embodiments, only one single row of light beams can be used for each detector element.

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." Means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure, the terminology "orbit" encompasses, among other things, a path fully around an object, such as, e.g., a patient or a path only partially around an object, such as, e.g., a patient.

What is claimed is:

1. A non-circular-orbit detection method, comprising:
    locating first and second detectors, displaced with respect to one another, a distance from a patient;
    moving the first and second detectors in a direction towards said patient until a first sensor senses a first point of said patient at a first sensing position;
    storing said first sensing position;
    moving the first and second detectors in a second direction from said first sensing position until a second sensor senses a second point of said patient at a second sensing position;
    storing said second sensing position;
    calculating a non-circular orbit about said patient using said stored first and second sensing positions; and
    moving the first and second detectors in a non-circular-orbit about said patient.

2. The method of claim 1, further including determining the non-circular-orbit based on locations of said first point and said second point.

3. The method of claim 1, further including determining the non-circular-orbit based on locations of said first point, said second point and a third point on a surface the patient contacts during detection.

4. The method of claim 1, further including having said first and second detectors include nuclear medicine detectors.

5. The method of claim 1, further including locating said first and second detectors at an angle with respect to one another.

6. The method of claim 1, further including locating said first and second detectors at an angle of about 90 degrees from one another.

7. The method of claim 1, wherein said first direction is generally downward.

8. The method of claim 7, wherein said first direction is generally vertical.

9. The method of claim 1, wherein said second direction is generally parallel to a front of said first detector.

10. The method of claim 1, wherein said first and second sensors emit light beams that are broken by proximity to a patient.

11. A method for orbital calculation, comprising:
    a) moving, relative to a patient, a first detector in a first direction toward said patient to a position adjacent to said patient based on an output of a sensor that senses patient proximity to said first detector;
    b) moving, relative to the patient, a second detector in a second direction toward the patient to a position adjacent to said patient based on an output of a sensor that senses patient proximity to said second detector;
    c) calculating an orbital path of said first and second detectors around the patient based upon said position adjacent to said patient in part a) and said position adjacent to said patient in part b);
    d) using said calculated orbital path to move said first and second detectors about said patient to obtain image data of said; and
    performing said moving in parts a) and b) automatically.

12. An orbital-detector apparatus, comprising:
    a) a first detector element to detect inside a patient;
    b) a first sensor element to sense patient proximity to said first detector element;
    c) a second detector element to detect inside the patient;

d) a second sensor element to sense patient proximity to said second detector element;

e) a first carrier mechanism configured to move said first detector element in a first direction from a position distal to the patient to a first position adjacent to said patient based on an output of said first sensor element;

f) a second carrier mechanism configured to move said second detector element in a second direction from a position distal to the patient to a second position proximate to said patient based on an output of said second sensor element;

g) a control unit configured to calculate an orbital path of at least one of said first detector element and second detector element around the patient based upon said first and second positions;

wherein front surfaces of said first detector element and said second detector element are at an angle of substantially 90 degrees from one another, and wherein said first direction is substantially downward and vertical.

13. The apparatus of claim 12, wherein said orbital path is a non-circular orbit.

14. The apparatus of claim 12, wherein said apparatus is a nuclear medicine imaging apparatus.

15. The apparatus of claim 12, wherein said apparatus varies a radius of said orbital path to reduce a distance of said first and second detector elements from the patient.

16. The apparatus of claim 12, wherein at least one of said first detector element and said second detector element includes a parallel-hole collimated detector.

17. The apparatus of claim 12, wherein said second direction is substantially parallel to a front of said first detector element.

18. The apparatus of claim 12, wherein said first sensor element emits a light beam that is broken by proximity to a patient.

19. The apparatus of claim 12, wherein said second sensor element emits a light beam that is broken by proximity to a patient.

20. A non-circular-orbit calculator, comprising:

a) first and second detector elements arranged in a generally V-configuration with said first detector element extending along one leg of said V-configuration and said second detector element extending along another leg of said V-configuration;

b) means for moving said first and second detector elements, relatively to a patient, such that an open end of said V-configuration moves towards said patient until a sensor associated with said first detector element senses a first point of the patient;

c) means for moving said first and second detector elements, relatively to said patient, generally parallel to said one leg of said V-configuration until a sensor associated with said second detector element senses a second point of the patient;

d) means for storing positions of said first and second detector elements when said sensors respectively detect said first and second points of said patient; and e) means for calculating a non-circular orbit about said patient based on said stored positions of said first and second detector elements.

21. The apparatus of claim 20, further including means for moving said first and second detectors in a non-circular orbit about said patient based on said first and second points.

22. A method for nuclear medicine imaging with at least one nuclear medicine detector that follows a non-circular orbit, comprising:

a) automatically determining a plurality of orbital locations around a perimeter of a patient before performing image data acquisition;

b) automatically predetermining a non-circular orbit around a patient based, at least in part, upon said plurality of locations;

c) moving at least one nuclear medicine detector along said predetermined non-circular orbit around said patient for acquisition of nuclear medicine data.

23. The method of claim 22, wherein said automatically determining in a) includes determining the locations by sensing a proximity to a patient of at least two detectors which are arranged in a V-configuration during data acquisition.

24. The method of claim 23, wherein said automatically determining in b) includes calculating a non-circular orbit using a controller.

25. The method of claim 22, wherein said automatically determining in a) includes establishing at least one location based on at least one location against which the patient is supported.

* * * * *